United States Patent [19]

Feddersen et al.

[11] Patent Number: 5,257,202

[45] Date of Patent: Oct. 26, 1993

[54] METHOD AND MEANS FOR PARALLEL FREQUENCY ACQUISITION IN FREQUENCY DOMAIN FLUOROMETRY

[75] Inventors: Brett A. Feddersen; Enrico Gratton, both of Urbana, Ill.; David W. Piston, Ithaca, N.Y.

[73] Assignee: Research Corporation Technologies, Inc., Tucson, Ariz.

[21] Appl. No.: 619,290

[22] Filed: Nov. 27, 1990

Related U.S. Application Data

[63] Continuation-in-part of Ser. No. 310,404, Feb. 13, 1989, abandoned.

[51] Int. Cl.$^5$ .............................................. G01N 21/64
[52] U.S. Cl. ..................................... 364/498; 356/317; 250/458.1
[58] Field of Search ........... 364/498, 553, 554, 728.03; 356/317, 318; 250/458.1

[56] References Cited

U.S. PATENT DOCUMENTS

| | | | |
|---|---|---|---|
| 4,840,485 | 6/1989 | Gatton | 356/317 |
| 4,855,930 | 8/1989 | Chao et al. | 250/458.1 |
| 4,937,457 | 6/1990 | Mitchell | 250/458.1 |

Primary Examiner—Edward R. Cosimano
Assistant Examiner—Ellis B. Ramirez
Attorney, Agent, or Firm—Scully, Scott, Murphy & Presser

[57] ABSTRACT

A digital frequency domain fluorometer utilizing a computer-controlled digital data acquisition system is use for the study of fluorescence and phosphorescence phenomena in the bio-chemical, biological and bio-physics arts. The computer is used for the direct collection of data, as well as for the filtering and calculation of the phase and modulation values of the sample under study. From these values, fluorescence lifetimes and anisotropy decay times can determined. The digital data acquisition system provides for the simultaneous collection and processing of several modulation frequencies. In addition, the digital frequency domain fluorometer can utilize an array detector for detecting the modulated light from the various samples under study. The use of the array detector provides a means for independently collecting data over a large number of pixels. This configuration allows for a time resolved image to be collected at once.

65 Claims, 7 Drawing Sheets

METHOD AND MEANS FOR PARALLEL FREQUENCY ACQUISITION IN FREQUENCY DOMAIN FLUOROMETRY

GOVERNMENT SUPPORT

The invention described herein was made in connection with work performed under a grant or award from the Division of Research Resources of the National Institute of Health.

This application is a continuation-in-part of copending application Ser. No. 310,404 filed on Feb. 13, 1989, now abandoned.

BACKGROUND OF THE INVENTION

1. Field of the Invention

The present invention relates to the field of analytical chemistry, and particularly to the study of fluorescence and phosphoresence phenomena in the biochemical, biological and biophysical arts.

2. Discussion of the Prior Art

The use of fluorescence spectroscopy for the study of the dynamics of macromolecules is becoming more widespread as more sophisticated instrumentation is being developed. Although fluorescence spectroscopy has developed into a widely accepted technique in the physical and chemical sciences as well as in the biological sciences, the practical utility of fluorescence methods is still limited by the availability of fluorescence spectroscopy instrumentation capable of measuring such events accurately.

Fluorescence is the rapid decay from a higher to a lower state of the same multiplicity. The natural time window of fluorescence is suitable to resolve dynamic events occurring in the nanosecond (ns) to pico-second (ps) time region. The above characteristics, coupled with the sensitivity of the excited state of a fluorophore to the physicochemical properties of its environment, is a major reason why fluorescence spectroscopy techniques are so frequently used in the study of micro-biological structures and functions.

The greatest interest is in measuring dynamic events displayed in the kinetics of intensity decay (fluorescence lifetimes) and anisotropy decay. The fluorescence lifetime reflects not only the intrinsic radiative rate of the excited state, but also the interactions of the fluorophore with the environment. Anisotropy decay measures the displacement of the emission transition dipole with time after excitation and thus reflects the rotational motion of the fluorophore. The rate and the amplitude of the rotational motion in a given time are themselves dependent on the free volume, the microscopic viscosity of the local environment and the forces acting on the excited molecule. Therefore, anisotropy decay indirectly describes the structure and dynamics of the fluorophore's environment. Clearly, a detailed study of the fundamental fluorescence observables (spectrum, quantum yield, lifetime and anisotropy) can provide substantial information about a biological macromolecule and its surrounding. Additional insight can be gained, if the system is physically or chemically perturbed, for example, by temperature or viscosity change or the presence of fluorescence quenching agents. The frequently complex fluorescence signal from biological systems does not easily yield to mathematical analysis and it may be difficult to correlate a physical event with the result of the analysis.

The time decay of fluorescence is usually measured using one of two accepted, but different approaches. Measurements of fluorescence decay can be made in the time domain using the popular technique of correlated single photon counting (SPC), or in the frequency domain by determining the phase delay and the relative modulation of the fluorescence signal with respect to the exciting light. The modern study of fluorescence properties started with time domain fluorometry and has evolved into methods using frequency domain fluorometry. In the frequency domain, the frequency axis is examined one point at a time, while in the time domain, the full decay is collected at once; however, the collection of information in the time domain takes from several minutes to several hours depending upon the excitation source, while in the frequency domain, the data collection at a single frequency takes only a few seconds. Therefore, it is possible in the frequency domain to acquire an equivalent amount of information in a similar amount of time. Indeed, a great advantage in the frequency domain can be achieved if all frequencies can be collected at the same time.

The maximum time resolution of sequential multifrequency phase fluorometers is about 1 or 2 picoseconds, which compares favorably with time correlated single photon counting instruments. The decomposition of the decay curve using a sum of exponentials, may also be obtained from a multifrequency measurement applying a non-linear least squares routine. The analysis of a double and triple exponential decay may be performed on dedicated micro-computers.

Resolution of emission anisotropy decay is obtained by a measurement of the differential phase and modulation ratio of the horizontally and vertically polarized emission components, arising from vertically polarized excitation. This technique, originally developed for single modulation frequency operation, has become extremely powerful when coupled with a multifrequency phase fluorometer. Fast rotational correlation times on the order of 10 picoseconds and longer can be measured. Resolution of anisotropic rotational motions can also be obtained from a multifrequency data set using a non-linear least squares analysis. Restricted rotational motions can also be analyzed. The ability to perform direct differential measurement, such as the phase delay between the perpendicular and the parallel polarized components of the emissions, is a unique intrinsic characteristic of phase fluorometry and results in an improved time resolution.

Phase fluorometry has the intrinsic capability to perform phase sensitive detection, which provides a simple and powerful method to separate spectral components in a mixture of fluorophores. This separation is based on the principle that each emitting species in the mixture has a characteristic phase delay. The spectra of the overlapping components can be obtained with a single scan using our new approach of phase and modulation resolved spectra. This simple approach requires no fitting of the data. The resolution is instead obtained directly from the values of the phase and modulation.

The prior art shows a number of examples of systems utilizing frequency domain fluorometry techniques. The 1984 article "The Measurement and Analysis of Heterogeneous Emissions by Multi-frequency Phase and Modulation Fluorometry" by Jameson, Gratton, and Hall, *Applied Spectroscopy Reviews*, 20(1), pages 55–106 (1984) discloses two methods of multi-frequency phase and modulation fluorometry as well as a commercially available fluorometer. In addition, the article discloses a fluorometer the authors developed for research purposes. The commercially developed fluorometer, developed by SLM AMINCO, utilizes a xenon arc lamp to provide an excitation signal to generate the fluorescence emissions. The light supplied by the arc lamp is intensity modulated before impinging upon a sample to be studied. The light emitted by the (study) sample is detected by a photomultiplier, the second or third dynode of which is modulated at a frequency equal to the light modulation frequency plus a small additional frequency. This procedure is a cross-correlation technique, wherein the phase and modulation information of the emitted signal is transposed to a much lower frequency range where it can be interrogated. The phase delay and demodulation of the emitted signal relative to the scattered light is then calculated. The research fluorometer described in the article is a variable frequency cross-correlation phase fluorometer which utilizes an argon ion laser to provide an excitation beam to excite the fluorescence action and to provide a reference signal. The light supplied by the laser is sinusoidally modulated, and split into two beams, one signal is used to excite the study sample and the second signal is used as the reference signal. The reference signal and the signal emitted by the study sample are then passed through two photomultipliers wherein the cross-correlation processing described above is done. The outputs from both photomultipliers are then passed through identical sections of analog circuitry wherein the data is sequentially processed and displayed.

The 1986 article "A Multi-Frequency Phase Fluorometer using the Harmonic Content of a Mode Locked Laser" by Alcala and Gratton, *Analytical Instrumentation*, 14(3 and 4), pages 225–250 (1985) discloses a cross-correlation phase and modulation fluorometer which utilizes the harmonic content of a high repetition rate, mode locked laser. In the frequency domain a pulsed source provides a large series of equally spaced harmonic frequencies. The pulses from the laser are amplitude modulated and frequency doubled. The signal is then split into a reference beam and an excitation beam. The reference beam is directed to a first photomultiplier and the excitation beam is directed to a study sample and then the emission from the sample is detected by a second photomultiplier. The photomultipliers provide cross-correlated mixing which in addition to frequency translation also allows transfer of the phase and modulation information desired at the individual harmonic frequencies. The outputs from the photomultipliers are then passed through various forms of analog filtering circuits and amplifiers wherein the necessary phase and modulated data is sequentially derived from the outputs of the photomultipliers.

Frequency domain fluorometry in certain instances has the advantage of the rapid determination of single or double exponential fluorescence lifetimes which can be obtained by measurements at only one or two frequencies. This is not possible for systems where complex fluorescence decays must be resolved. In order to handle complex decays, a large number of modulation frequencies is needed to obtain the full decay information. The above disclosed fluorometers provide this capability only to a limited extent.

The above referenced articles disclose fluorometers that use frequency domain techniques as opposed to time domain techniques. Frequency domain fluorometers have the advantage of high accuracy and rapid determination of fluorescence lifetimes. However, the above referenced fluorometers utilize analog signal processing techniques after data collection. Unwanted effects on the signals of interest are caused by the bandwidth and non-linearity of the analog filters used in the above referenced fluorometers. In the analog electronics of most commercial frequency domain fluorometers, six pole active filters are utilized to perform the necessary filtering functions. These filters are hard to tune to the appropriate frequency, they suffer from thermal and drifting problems and have undesirable phase shift. The accuracy of lifetime measurement is limited by the analog signal processing portion of the fluorometers.

SUMMARY OF THE INVENTION

The present invention utilizes a computer controlled digital acquisition system to create a parallel phase fluorometer which collects and processes several harmonic frequencies simultaneously. The digital processing functions used in the present invention provide for more accurate filtering functions, parallel frequency acquisition, and the ability to change filter functions in software at minimal cost and requiring only a minimal time.

The present invention is directed to a digital frequency domain fluorometer for measuring the fluorescence response of a sample when excited by a pulsed light source. The invention is basically comprised of two sections. The first section is a novel data acquisition section which is capable of collecting spectral components of fluorescence data in an x-y array. The second section is a parallel phase fluorometer processing section which is responsible for simultaneous processing the collected data value and to provide useful information to the operator.

The data acquisition section basically involves exciting a sample to be studied so as to cause the sample to emit a fluorescent light. In one embodiment of the invention, the emitted fluorescent light is captured and down converted to a more manageable frequency using the sample and reference photomultiplier tubes which mix a cross-correlation frequency therein. The correlation signal from the PMT is now an electric signal as opposed to a light signal. The phase and modulation information from the response of the sample is carried by a discrete waveform at the correlation frequency, and may be processed by the parallel phase fluorometer processing section of the invention.

In a second embodiment, a diode or CCD array is coupled with a gatable means to analyze the spectral and frequency response of the sample at discrete x-y locations. The apparent time resolution of the diode array is enhanced by a unique gating technique which cross-correlates a high frequency source at $f_1$ with an image intensifier at $f_1 + f_c$ to optically cross-correlate the emission response phase and modulation information onto $f_c$. This technique enables an array, which nominally resolves in the milli-second range, to time resolve events in the picosecond range, since the frequency to be resolved which is $f_1$, has been translated to $f_c$ by the gating action of the image intensifier.

The parallel phase fluorometer processing section takes the discrete waveform from either of the above embodiments and digitally filters and processes it to extract the desired information. The desired information consists of modulation and phase data with respect to the reference signals. The digital filtering is done in software using digital filtering techniques including averaging filtering and fast Fourier transforms (FFT).

The digital frequency domain fluorometer of the present invention provides for the filtering and calculation of the phase and modulation ratio of a fluorescence signal from which the fluorescence lifetime of the decay can be determined. In addition, by incorporating a computer for the direct collection of data and for the processing of the data, the majority of systematic errors due to analog signal processing circuits can be avoided or minimized. The digital acquisition method described herein allows for much better signal filtering than the analog electronics currently used in frequency domain fluorometers and also provides for the added capability of parallel frequency acquisition.

Among the advantages of the digital electronics is the intrinsic capability to modify the base filter frequency by simply entering into the computer a different number for the acquisition period. In this manner, it is possible to determine the best cross-correlation frequency to be used on the basis of the phase noise characteristic of the frequency synthesizer.

The cost of the digital acquisition system is substantially reduced relative to the cost of standard analog systems. The off the shelf digitizing board used in the to at least described embodiment costs about $1,000, compared $10,000 for the analog electronics found in commercial frequency domain fluorometers.

The improvements given by this new digital electronic acquisition system can be summarized as: (1) a factor of 10 in enhancement of filtering capabilities; (2) a factor of 10 in reduction of acquisition time; and (3) a factor of 10 in reduction of cost.

The present invention provides a new and practical means to analyze complex fluorescence decays in real-time using standard data collection techniques and digital processing techniques. The invention is useful in the analysis of multi-exponential decays, continuous lifetime distributions, rotational rate determinations, resolution of spectral components, excited state reactions and energy transfer and dipolar relaxations.

BRIEF DESCRIPTION OF THE DRAWINGS

FIG. 3 is a schematic illustration of a current to voltage converter and amplifier used to match the output of the PMT tubes to a standard analog to digital converter.

DESCRIPTION OF THE PREFERRED EMBODIMENT

Figure 1:
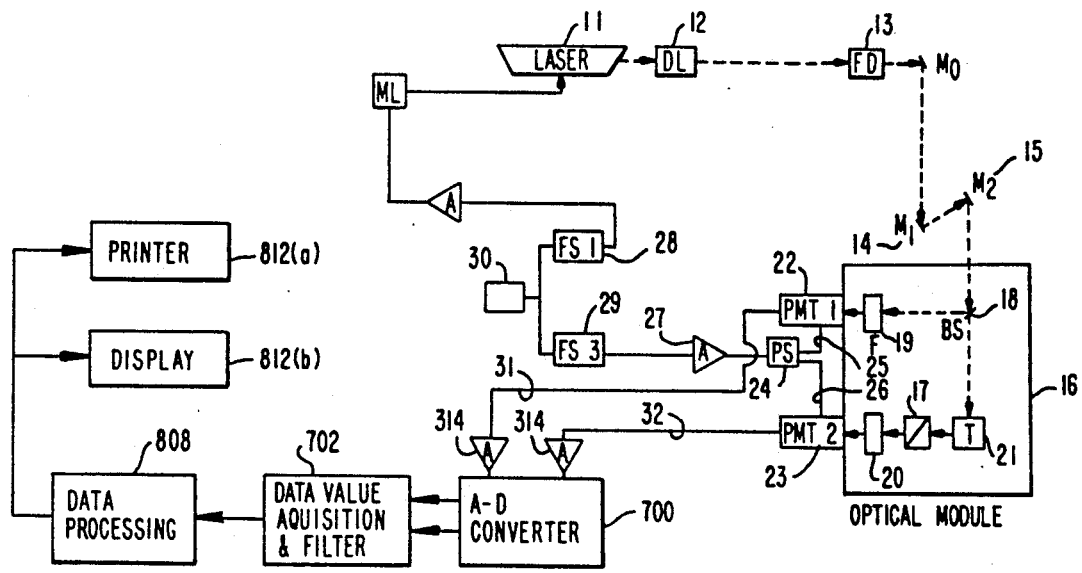
FIG. 1 is a diagrammatic illustration of one embodiment of our invention using photomultiplier tubes for cross-correlation mixing.

The present invention relates to improvements in the field of frequency domain phase fluorometry. In one embodiment, a pulsed light source having a predetermined frequency and multiple harmonics is used to simultaneously excite a sample at a fundamental and a plurality of harmonic frequencies. Improved digital acquisition and cross-correlation techniques enable the collection of the phase and modulation information at each of the frequencies onto a single wave form. The wave form is digitally filtered to remove non-harmonic and non-synchronous frequencies, and a fast fourier transform is performed on the filtered waveform.

The result is the simultaneous derivation of the phase and modulation values of the sample response at a plurality of frequencies from a single excitation.

In a second embodiment, the first embodiment is used with an array detector capable of collecting discrete values of the phase and modulation response at a plurality of x-y locations, and at a plurality of various wave length or color emissions to assist in resolving and imaging multiple emissions from a single excitation.

The array detector provides an improvement over known array devices in as much as it enables measurements of the luminescence decay time in the pico-second to nano-second range over the entire spectral emission band using correlated gating techniques. The gating reduces the duty cycle of the measurement, and extends the maximum resolution time to about 20–30 pico-seconds with a duty cycle of about 50%.

MULTI FREQUENCY PHASE FLUOROMETRY

The time decay of fluorescence is typically measured using one of two different approaches. The system response to transient (pulsed) excitation can be determined in the time domain by the popular technique of time correlated single photon counting. Alternatively, the fluorescence response can be measured in the frequency domain, by determining the phase delay and the relative modulation of the fluorescence signal with respect to the exciting light. The time domain and frequency domain approaches provide equivalent information and are related to each other by the fourier transform.

In the frequency domain the time variation of the excitation light intensity is described by $$E(t) = E_o(1 + M_e \sin(wt)) \qquad (1)$$

where $E_o$ and $M_e$ are the average value of the intensity and the modulation of the excitation respectively. The overall fluorescence response of the system to sinusoidal excitation can be written in the form $$F(t) = F_0[1 + M_f \sin(wt-\phi)] \quad (2)$$

Where $F_o$ and $M_f$ are the average value of the intensity and the modulation of the fluorescence, respectively. For linear systems the emitted fluorescence has the same modulation frequency but is demodulated and phase-shifted with respect to the exciting light. The phase delay and modulation ratio between the excitation and the emission constitute the two independent measurable quantities in phase fluorometry. The following equations relate these parameters to the case of the pulse response, $I_F(t)$, to excitation by a delta function at excitation frequency, w, $$\tan \phi = \frac{S}{G} \quad (3)$$

$$M = \frac{M_f}{M_e} = N^{-1}(S^2 + G^2)^{\frac{1}{2}} \quad (4)$$

where $$S = \int_0^\infty I_F(t)\sin \omega t \, dt \quad (5)$$

$$G = \int_0^\infty I_F(t)\cos \omega t \, dt \quad (6)$$

$$N = \int_0^\infty I_F(t) dt. \quad (6)$$

Knowledge of $\phi$ and M is equivalent to knowledge of the functions S and G which correspond to the sine and cosine fourier transforms of the ideal pulse response $I_F(t)$. Consequently the measurement of phase and modulation as a function of the frequency is equivalent to determining the time evolution of the emitting system to delta pulse excitation. In phase-modulation fluorometry, however, deconvolution for the finite width of the excitation pulse and the time response of the detection system is unnecessary since the ideal pulse response is obtained.

Multiple frequency excitation has traditionally been accomplished by using a synchrotron or pulsed laser output at a plurality of frequencies. It is also known that pulsed light sources contains multiple harmonics, and that in the frequency domain all of the photons in the light source contribute to the measurement of each harmonic frequency. The average signal measured at the i-th harmonic for very narrow pulses has practically the same intensity as the complete fluorescent signal.

Since the use of the preselected fundamental and harmonic frequencies obviates the need for sequentially collecting separate measurements at each frequency, and the attendant needs to tune and acquire "dark wave" reference signals at each frequency, its use is preferred in the practice of this invention, except where the measurement of fluorescent lifetime or rotational rate requires the use of a frequency available only from a modulated source.

The Principle of Cross-Correlation Parallel Phase Fluorometry

Cross-correlation in a phase fluorometer was first described by Spencer and Weber in an article entitled "Measurements of Sub-nano-second Fluorescence Lifetime with a Cross-Correlation Phase Fluorometer", Ann. New York Acad. Sci. (1969) p361. In the present invention, the operating principle in the same, but it is extended to cover the harmonics in the cross-correlation signal. When a fluorophore is excited by a pulsed light source, the fluorescence has the same frequencies as the excitation, but each harmonic frequency is demodulated and phase shifted differently with respect to the exciting light. The modulation ratio, M, and the phase shift, $\phi$, are related to the fluorescence lifetime, $\tau$, by $$\tan \phi = w\tau \quad (7)$$

$$M = \frac{M_f}{M_e} = \frac{1}{(1 + (w\tau)^2)^{\frac{1}{2}}}$$

where $M_f$ and $M_e$ are the modulation of the fluorescence and the excitation respectively. The frequency content of the fluorescence can be written as $$F(t) = F_0\left[1 + \sum_{n=1}^{N} M_{fn}\cos(nwt + \phi_n)\right] \quad (8)$$

where $F_0$ is the average fluorescence. The cross-correlation technique mixes the fluorescence signal with a cross-correlation signal, C(t), which is at a slightly different base frequency, $W_c$:

$$C(t) = C_0\left[1 + \sum_{k=1}^{K} M_{ck}\cos(kw_c t + \phi_k)\right] \quad (9)$$

the resulting signal is the product of $V(t) = F(t) \cdot C(t)$.

$$V(t) = F_o C_o \left[\left(1 + \sum_{n=1}^{N} M_{fn}\cos(nwt + \phi_n) + \right.\right. \quad (10)$$

$$\sum_{k=1}^{K} M_{ck}\cos(kw_c t + \phi_k) + \sum_{n=1}^{N} M_{fn}\cos(nwt + \phi_n) +$$

$$\left.\left. \sum_{k=1}^{K} M_{ck}\cos(kw_c t + \phi_k) \right)\right].$$

The last term can be rewritten using trigonometric relationships as the sum and difference of the two frequencies. If we look at only the lowest frequency region, with i=j, the only term remaining is:

$$\sum_{n=1}^{K} \frac{M_f M_e}{2} \cos(n\Delta wt + \Delta\phi). \quad (11)$$

where $\Delta w = w_c - w, \Delta\phi = \phi - \phi_j$. This series ends at n=K since we have assumed K N, i.e. the cross-correlation signal has less harmonic content than the fluorescence signal. This expression contains all of the phase and modulation information of the original fluorescence signal at all the harmonic frequencies, now as harmonics of $w_c$, but if $w_c$ is very close to w, then this information is at much lower frequencies that are easier to isolate and sample with our digital electronics. In the embodiment illustrated in FIG. 1, $\Delta f$ was set to 40 Hz. In the embodiment illustrated in FIG. 2, $\Delta f = w/2\pi$ is set to 15 to 7.5 Hz.

For parallel phase fluorometry, a high harmonic content in both the light modulation and in the cross-correlation signal is required High repetition pulsed sources, such as mode-locked lasers and synchrotron radiation, intrinsically contain a high harmonic content. Traditionally, the cross-correlation product is obtained by applying an appropriate voltage to one of the dynodes of the photomultiplier tube. This internal mixing is quite powerful, since the PMT itself is a very good mixer. The PMT dynode chain produces good amplification with very low noise, and it does not require any extra components. In the embodiment illustrated in FIG. 1, the mixing occurs in the photomultiplier tube. In the embodiment illustrated in FIG. 2, the mixing occurs in the light signal emitted by the sample by a gating technique, prior to the sampling by the diode array. A more complete explanation of the cross correlation accompanies the detailed description of each embodiment.

PARALLEL PHASE FLUOROMETER

The parallel phase fluorometer illustrated in FIG. 1 has the intrinsic capability to separate out all of the harmonic information contained in the cross-correlated signal. This capability can be exploited by using a light source that has high harmonic content, such as a pulsed laser system, or by pulsing the Pockel's cell modulator used in most phase fluorometers and cross-correlating with a waveform that contains harmonics. A mode-locked laser system is also known to have a frequency content of several gigahertz, and pulsing other light modulation systems can increase their frequency content. Laser diodes and high speed light emitting diodes intended for use with fiber optics may also be used to generate a pulsed wave form with a high harmonic content.

By using a light source with an intrinsic high harmonic value, the total data acquisition time can be greatly decreased by simultaneously acquiring many frequencies. In the embodiment illustrated in FIG. 1, laser 11 is a mode locked Nd-YAG laser which synchronously pumps a cavity dumped dye laser 12 (Antares model, 765-700 Coherent). The pulse train output is frequency doubled to UV light by using a frequency doubler 13, Coherent model 7049.

This laser system can cover the wavelength range from 265 nm to 850 nm by changing the laser dyes and the doubler crystal. The repetition frequency of the laser is normally set from 1 to 2.00 MHz. All harmonics of the basic frequency can be used up to about 4to 6 GHz, (a limit imposed by present synthesizers and radiofrequency amplifiers). If a lower modulation frequency is required, the cavity dumper can be set to any integral submultiple of 1 MHz, up to a single pulse operation.

The polarization of the dye laser light is vertical relative to the laboratory axis while the UV output from the doubler 13 is horizontally polarized. The plane of polarization of the UV beam is rotated to 35 degrees from the vertical (the ideal polarization angle for lifetime measurements) using an arrangement of two mirrors. The mirrors 14, 15 which not only change the polarization angle of the exciting light but also steer the beam into the optical module 16, and have a metallic coating (Melles Griot coating 028); since a dielectric coating would give rise to a wavelength and polarization dependent reflection. The emission of the sample may be polarized by polarizer 17 for measurement and study of anisotropic decay. The optical module 16 also includes a quartz beam splitter 18, filter holders 19, 20 and a sample receiving holder 21.

Hammamatsu R928 photomultiplier tubes 22,23 are selected because of their wide-range wavelength sensitivity, high gain, low price and relatively small color effect.

The modulation of the PMT tubes 22,23 is obtained by application of an alternating voltage to the second dynode D2 through a power splitter 24, as illustrated at 25,26. The characteristic curve of the PMT has a sharp rise, then the current reaches a maximum and decays again as the absolute voltage of the dynode increases. In order to modulate the gain of the PMT an RF voltage of about 40 V peak to peak is needed corresponding to an average power of 2 to 3 W on a 50 ohm terminator. The RF voltage is provided by an RF amplifier 27 (ENI Model 603L.)

Instead of attempting to acquire the entire frequency range in one measurement, we acquire the range from 1 MHz to 500 MHz in three steps. The laser is mode locked at $F_1$ by frequency synthesizer 28, while the PMT's are pulsed at $F_1+40$ Hz, 40 Hz is the cross frequency synthesizer 29. The synthesizers 28,29 are maintained in a phase locked loop figuratively illustrated at 30. In normal operation, the synthesizer 28, is set at a frequency of 1 MHz with a pulse width of 100 ns. Synthesizer 29 is set at 1 MHz+40 Hz. The pulse width is 100 ns.

The duty cycle becomes 1/10 with a reduction of only a factor of 5 with respect to the standard single frequency mixing (duty cycle ½). Using this pulsed cross-correlation signal, about nine different frequencies can be easily collected in the range from 1 to 9 MHz. Then, the base frequency of the synthesizers are set at 10 MHz, and 10 MHz+40 Hz with a pulse width of 10 ns and the duty cycle is still 1/10. Again, frequencies are collected in the range from 10 to 90 MHz. Finally, the base frequency of the synthesizers are set at 100 MHz and. 100 MHz+40 Hz and the pulse width to about 2 ns and frequencies are collected from 100 MHz up to about 500 MHz. This frequency limit is imposed by the PMT detectors and by the fluorescence characteristic of the emitting substance. The reduction in acquisition time with respect to the prior art sequential multi-frequency mode is about a factor of ten, since ten frequencies are collected simultaneously.

The output of PMT tubes 22,23 carry the phase and modulation information imparted by the sample on a correlation frequency of 40 Hz. The cross-correlation current signal on signal lines 31, 32 is first converted to a voltage signal, and then amplified by amplifiers 314, as more fully explained with respect to FIG. 3. The amplified signals are then digitized at 700, as hereinafter explained.

THE DIGITAL ACQUISITION SYSTEM

In the digital acquisition system of our invention, most of the analog electronics have been eliminated. The only analog elements used are the current-to-voltage converters 300 needed to transform the output of the photomultiplier tubes to a voltage and the amplifiers 314, to boost the signal level. The current-to-voltage converter and amplifier are built directly into the empty slot of a commercially available data acquisition board. In one embodiment of the invention, a MicroWay A2D-160 board was used because of its speed, its two collection channels, and its use of the computer's direct memory access (DMA) capabilities. This board fits into a slot of any IBM-PC-compatible computer. Direct memory access relieves the central processing unit (CPU)

from processing data during the acquisition period, so that data collection and storage occur in the background. Therefore, the CPU is used only for the digital filtering processes and determination of the phase and modulation values of previously acquired waveforms. The CPU is free most of the time to run normal "housekeeping" tasks, such as displaying information on the status of the instrument. The A2D-160 board has a 12-bit analog-to-digital converter with a maximum sampling rate in single channel mode of 160 KHz. In our experience, 12-bits were always to obtain good accuracy. The actual resolution is improved due to the noise level of our signal. We have estimated that in our experimental condition we have about 15- to 16-bit effective resolution. With respect to the sampling rate, we are well below the board's limits. For the measurements reported here, we have used a sampling rate of 2.56 KHz.

Figure 3:
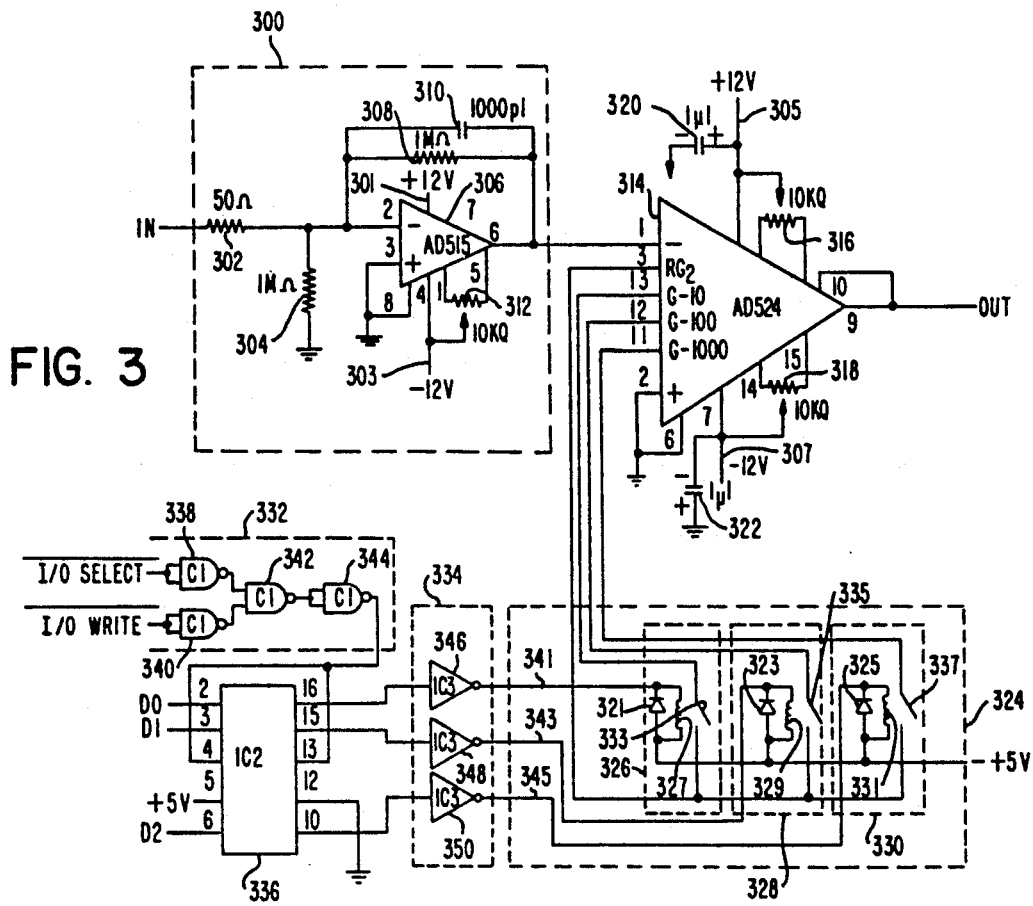
FIG. 3 is a diagrammatic illustration of a second embodiment for the improved array detector for optical cross-correlation mixing.

Referring now to FIG. 3 the analog circuitry is illustrated in schematic form. The output signals of the photomultiplier tubes enter the current-to-voltage converter 300 through a 50 ohm resistor 302 and a 1 megaohm resistor 304 to ground combination. The signal continues through this combination to an active low-pass filter comprised of an operational amplifier 306 with a negative feedback path comprised of a parallel combination of a 1 megaohm resistor 308 and a 1000 picoforad capacitor 310, the effect of which is to attenuate higher frequency signals. The operational amplifier is powered by a positive 12 volt signal 301 and a negative 12 volt signal 303. A variable 10 kilo-ohm resistor 312 is used to adjust the zero offset of the operational amplifier 306. The operational amplifier 306 used is an AD515 manufactured by Analog Devices, Inc.

The output of the current-to-voltage converter 300 is then directed to a variable gain amplifier 314. The variable gain amplifier 314 is capable of amplifying the output of the current-to-voltage converter 300 by a magnitude of 1, 10, 100 or 1000 times. The variable gain amplifier 314 is powered by a positive 12 volt signal 305 and a negative 12 volt signal 307. Adjustments to the variable gain amplifier 314 are made through a pair of 10 kilo-ohm resistors 316 and 318 which are connected to the positive and negative 12 volt signals and to ground through a pair of 1 microfarad capacitors 320 and 322. The value of the gain on the variable gain amplifier 314 is determined by a signal generated by a bank of relays 324.

The bank of relays is comprised of three independent relays 326, 328 and 330. The relays 326, 328 and 330 are controlled by digital logic circuitry comprised of three integrated circuits 332, 334 and 336. Each relay 326, 328 and 330 is comprised of a set of diodes 321, 323 and 325 a set of coils 327, 329 and 331 and a set of switches 333, 335 and 337. One side of each diode 321, 323 or 325 is connected to a positive 5 volt source 339 while the other side is connected to a digital integrated circuit 334 via lines 341, 343 and 345. When the value of any of the three outputs of integrated circuit 334 are logic 0, which corresponds to 0 volts, then that particular diode 326, 328 or 330 conducts current and magnetizes the particular coil 327, 329, 331 and thereby closes switches 333, 335 or 337.

The digital circuitry comprised of three integrated circuits 332, 334 and 336 control the gain on amplifier 314 by controlling the relays 326, 328 and 330. Integrated circuit 332 is a series of four NAND gates 338, 340, 342 and 344 which receive an I/O SELECT and I/O WRITE signal from the host computer. These two signals are used to latch the integrated circuit 336. Integrated circuit 336 receives three input signals D0, D1 and D2 from the host computer. These three signals are latched and stored in the integrated circuit 336 and are output to three inverters 346, 348 and 350 which are realized on one integrated circuit 334. By varying the possible combinations of D0, D1 and D2, the gain on the variable gain amplifier 314 can be altered. Table 1 given below contains the combinations of D0, D1 and D2 and the gains they cause to be made.

GAIN TABLE

| D2 | D1 | D0 | GAIN |
|----|----|----|------|
| 1 | 1 | 1 | 1 |
| 1 | 1 | 0 | 10 |
| 1 | 0 | 1 | 100 |
| 0 | 1 | 1 | 1000 |

In the digital acquisition system of the present invention, the host or controlling program is an adaptation of the standard acquisition software used in our laboratory and is available through Globals Unlimited, Department of Physics, UIUC. The program starts by initializing the hardware and setting up data files. First, the analog-to-digital board is disabled and the on-board timer is programmed. The A2D-160 card has a 4 MHz clock which is used by an AM9513 counter chip from Advanced Micro Devices. A "master reset" is issued to the AM9513, this resets and stops all counters; counter one is then loaded. This counter divides the 4 MHz clock to provide the appropriate sampling rate for the cross-correlated signal, which we have chosen to be at 40 Hz. Next, the DMA channel 1 of the IBM PC is masked, and programmed to transfer 2560 data points from the analog-to-digital card to a storage vector in the main computer memory. The 2560 data points represent 1280 data points per channel, which correspond to 32 data points per period for 40 periods. The 32-data-points-per-period was chosen because the highest harmonic that the fast fourier transform (FFT) algorithm, used by the filtering routine, can resolve is equal to half of the number of data points. The possibility to analyze up to the sixteenth harmonic was felt to be high enough for our application. This is not a limitation, because the number of data points per period can be increased with only a linear penalty of computation speed. The 40-period integration range was chosen because at the cross-correlation frequency of 40 Hz used in our instrument, data are collected in one second, and also for the efficiency of the filtering, which will be discussed later. Channel 3 on the PC interrupt controller is masked, and a new interrupt vector, pointing to a display and save routine, is loaded. When the timer, the DMA, and the interrupt controller have been programmed, the DMA and interrupt controller are unmasked, and the timer is started. The timer is free-running, so data are collected asynchronously.

Figure 7:
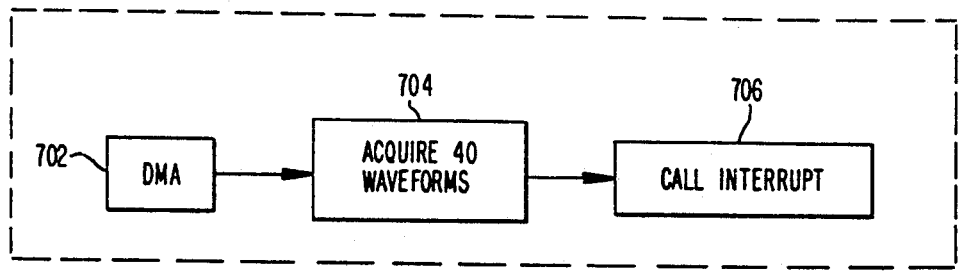
FIG. 7 is a conceptual illustration of the direct memory access portion of the invention.

The data collection proceeds, simultaneously converting both the excitation and emission channels by using the two independent sample-and-hold circuits, and is sampled by the 12bit analog-to-digital converter with a full scale range of −5 to +5 volts. As illustrated in FIG. 7, at the end of the conversion process the DMA 702 is addressed. The DMA then transfers the output of the analog-to-digital converter into the main memory of the computer as illustrated at 704; then the other sample-and-hold circuit is read, converted, and stored. The whole cycle is repeated until the 2560 data points are collected. Once the data has been stored, the DMA generates an end-of-process which triggers the interrupt routine indicated at 706. The interrupt routine 706 folds the 40 periods that arise from the one second integration into one, and then reduces the 32 data points into four bins, representing four phases of a period at the lowest harmonic frequency. The DC, AC, modulation, and phase of the waveform can be rapidly calculated from the values of the four bins. Those values are used only to give basic information "on the fly" for the data being collected. This information is displayed at the top line of the computer screen, and is updated every second. This information is useful to the user for continuous monitoring of the measuring conditions of the instrument. The interrupt routine reprograms the DMA and the interrupt controller and restarts the counter. The cycle starts again and is continuously repeated.

At the beginning of a measurement, the program sets the basic frequency of the synthesizer and asks for the reference lifetime value. A dark waveform is then digitized by repeating the interrupt cycle ten times. After the data have been collected, the averaged and folded waveform is analyzed by a FFT routine which provides additional filtering. The real and imaginary parts of the FFT are sufficient to calculate the AC, DC phase and modulation of up to the sixteenth harmonic. These values are subtracted from the sample and reference waveforms to reduce in-phase pickup noise. After the dark waveform is measured, the sample is illuminated and the fluorescence signal is acquired. The AC, DC, phase and modulation values are determined at the same moment. The reference compound (lifetime=ref) is then illuminated, and its AC, DC, phase and modulation values are calculated. When both the sample and reference have been collected, absolute phase and modulation values are calculated using the following expressions.

$$M_{corr} = \frac{M_{sam}}{M_{ref}} \frac{1}{(1 + w^2 \tau_{ref}^2)^{\frac{1}{2}}}$$

and $$\phi_{corr} = \tan^{-1}(W\tau_{ref}) + (\phi_{sam} - \phi_{ref}).$$

The sample is again illuminated, and its modulation and phase values are determined. Absolute phase and modulation values are then calculated using the new values of the sample modulation and phase and old reference numbers. The corrected modulation and phase numbers are averaged together, and the standard deviation is calculated. The reference sample is then illuminated and the cycle is repeated until the variance is below 0.2 degree and 0.004 for the phase and modulation, respectively.

Figure 8:
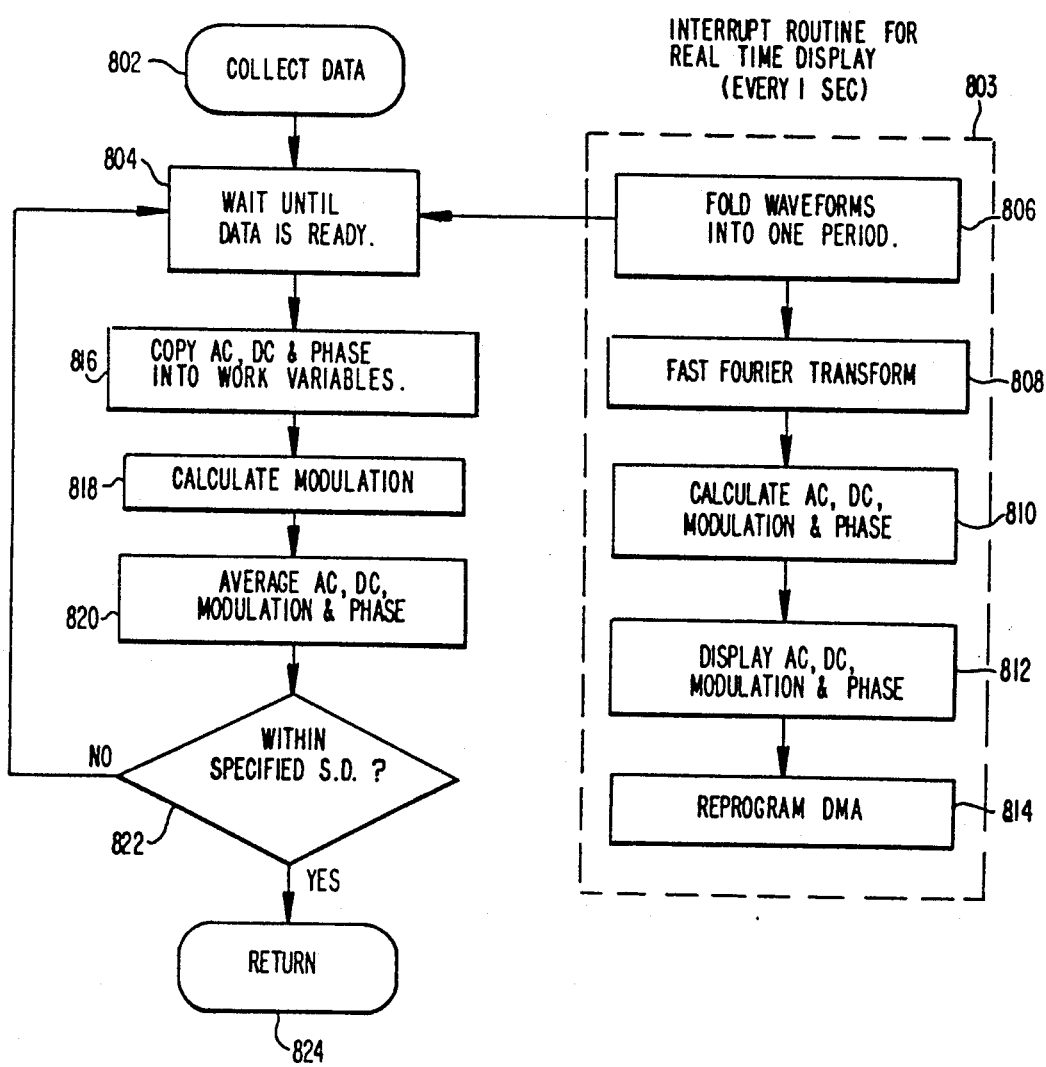
FIG. 8 is a simplified flow chart of the data acquisition and data processing programs used in the present invention.

This entire process is automatically controlled by the on-line computer using the Globals Unlimited software described above, as driven by the executive level software described in FIG. 8, and attached hereto as Appendix A.

Referring to FIG. 8, the entire procedure is shown in flow chart format. The data collection as described above is shown by block 802 of the flow chart. After the collection of data, the software checks to see if the EOP interrupt has been received thus indicating that the data is ready. This is represented by block 804 and corresponds to line 11 through line 40 on page 3 of the computer program listing as set forth in Appendix A. If the interrupt has been detected, the CPU transfers control to the interrupt routine indicated by the dotted box 803. The first box 806 represents the portion of the interrupt software that is responsible for folding the acquired waveform into one period of time, the reasons for this are explained earlier. The software that corresponds to box 806 is given in line 45 on page 3 of the computer program listing through line 2 on page 4 of the computer program listing. Block 808 represents the portion of software responsible for calculating the discrete fourier transform of the collected waveform. The software corresponding to box 808 is given in line 60 on page 10 of the computer program listing through line 60 on page 11 of the computer program listing. Block 810 represents the portion of the software that is used to calculate the DC, AC, modulation and phase of the wave form. The software corresponding to box 810 is given in line 65 on page 11 of the computer program listing through line 36 on page 12 of the computer program listing. Block 812 is a routine that displays the information calculated in block 810. The software corresponding to box 812 is given in line 20 on page 4 of the computer program listing through line 20 on page 5 of the computer program listing. The information is displayed at the top line of the computer screen, and is updated every second. Block 814 represents the software used to reprogram the DMA 702 shown in FIG. 7, the interrupt controls and it also restarts the internal counter. The software corresponding to box 814 is given in line 25 on page 5 of the computer program listing through line 20 on page 10 of the computer program listing. Upon completion of the routine described in box 814, the software is now returned to the main software routine Block 816 copies the information calculated by block 810 into new variables for further manipulation.

When both the sample and reference waveforms have been collected as described above, absolute phase and modulation values are calculated, which is represented by block 818. The corrected modulation and phase numbers are averaged together to form average values as is shown in block 820 The processing corresponding to boxes 816, 818 and 820 is done in a software loop given in line 60 on page 12 of the computer program listing through line 59 on page 13 of the computer program listing. After averaging the values together, the standard deviation is calculated and checked to see if it is in the specified range as shown in decision box 822. If standard deviation is not acceptable, the process of analyzing the data is repeated. If standard deviation is within tolerance, the software returns to its starting point, illustrated by block 824. The calculation of the standard deviation and the software corresponding to decision box 822 is given in line 61 on page 13 of the computer program listing through line 15 on page 14 of the computer program listing.

The digital acquisition system of the present invention excels at filtering. This operation must reject random and harmonic noise. Simulations show that if the second harmonic has an amplitude of 0.05 of the fundamental after the filtering, and is incorrectly associated with the first harmonic, the resulting phase measurement can be off by as much as five degrees. This is a very large error, and therefore the harmonics must be reduced to less than one part in 200 for the effect to be less than 0.2 degrees. In the standard analog electronics of most commercial frequency domain fluorometers, six pole active filters are used to perform the appropriate filtering. These filters are hard to tune, suffer thermal drifting problems, and have amplitude-dependent phase shifts, which become a problem if the sample and reference compounds do not emit nearly equal amounts of light. If this is the case, then the signal out of the PMT will have different amplitudes for the sample and reference cuvettes and the resulting phase-shifts from the filters will introduce a systematic phase deviation. The digital acquisition system of the present invention uses a sequence of two digital filters that do not suffer from these problems.

Figure 10A:
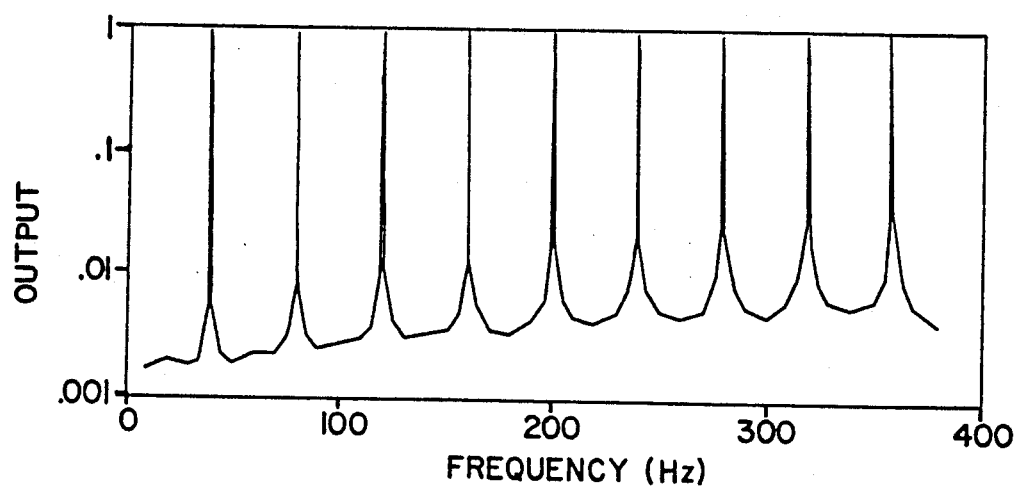
FIG. 10a is a graph illustrating the filter response of the digital averaging filter using 10 seconds of integration.

The first digital filter is the averaging filter. Since data are collected by acquiring 40 periods in a continuous stream and folding into one period, any frequency that is not a harmonic of the fundamental will destructively interfere with itself. Also, all signals which are not synchronous with the fundamental will average out. For example, if the fundamental is at 40 Hz and a 20 Hz signal is added, then in one 40 Hz waveform there is one-half of the 20 Hz waveform and the next 40 Hz waveform will contain the opposite half of the 20 Hz waveform. When the two waveforms are folded and added, the 20 Hz signal will cancel out exactly and the 40 Hz signal will remain. The filtering action of this filter depends on the number of waveforms collected and folded. The experimental filter response of our 40 waveform-averaging filter is shown in FIG. 10a. The points for this figure were obtained by applying a sinusoidal signal out of a HP3525 synthesizer directly to the A2D-160 board and then varying the frequency over the range specified in the Figure.

Figure 10B:
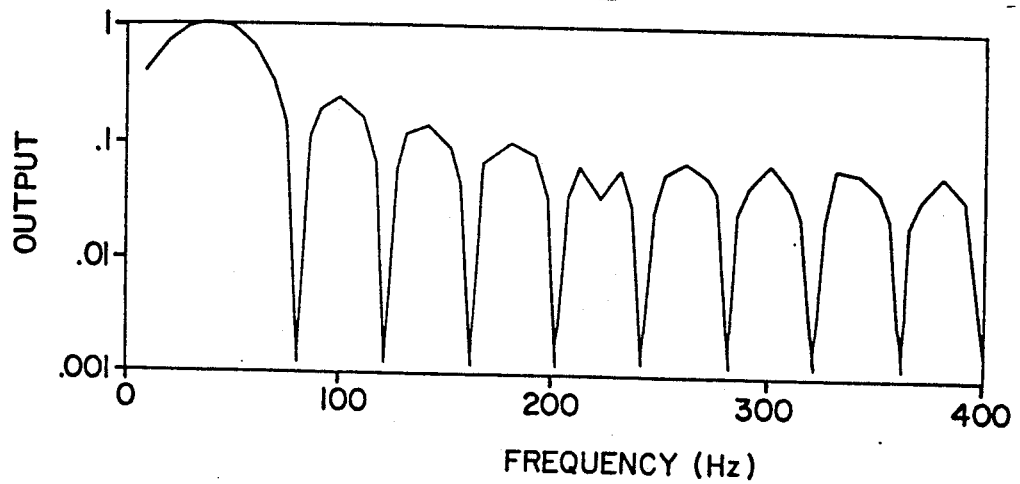
FIG. 10b is a graph illustrating the filter response of the fast fourier transform using only the fundamental frequency.
Figure 10C:
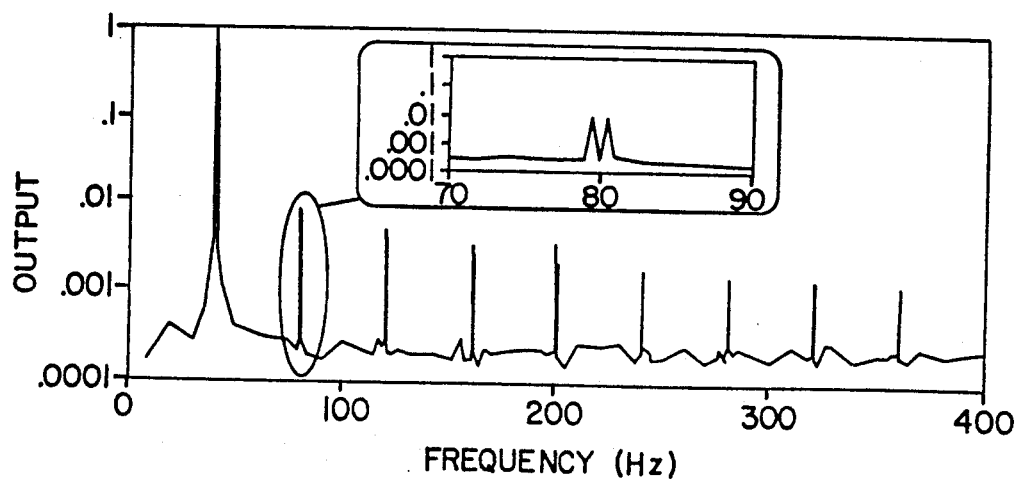
FIG. 10c is a graphic illustrating the response of the combined averaging filter and fast fourier transform calculated for the fundamental frequency.

An inherent property and, as we show later, an advantage of the averaging filter is that it lets the harmonics pass through. To separate the fundamental and the harmonic information, the averaging filter's output is processed by a FFT routine. The FFT routine also acts as a filter, because it resolves the input waveform to a DC value, the fundamental frequency, and its harmonics. Therefore, any of the harmonic frequencies can be rejected by simply ignoring its output from the FFT. The experimental filter response of the FFT, retaining the fundamental frequency only, is shown in FIG. 10b. The same signal as in FIG. 10a was used to obtain the experimental points in FIG. 10b. The FFT also provides the values needed to calculate the phase and modulation of the acquired waveform. The two filters, the averaging and the FFT, are in series and the final result is the product of the two filters. The total filter response, for the fundamental, is shown in FIG. 10c. As can be seen, the harmonics are rejected by more than a factor of 2,000. This is an improvement over the analog electronics of about a factor of ten.

To illustrate the advantages of the digital filter over the analog electronics, we used both methods to perform a series of measurements of phase and modulation values as a function of the amplitude of an input signal. The input signal was composed of a basic frequency of 40 Hz plus a uniform noise band limited to 1000 Hz of 100 mV amplitude. The signal at 40 Hz was varied in amplitude while the noise level was left constant. The phase of the reference with respect to the sample channel was 180° to avoid the indeterminate region of the 0° to 360° for the analog acquisition mode, which would introduce additional phase noise. Above 1 V signal, both methods provided an adequate response: the average deviation and the standard deviation of the phase value were within 0.1°, a value commonly considered adequate for frequency domain fluorometry. When the signal-to-noise ratio became smaller, the performance of the digital acquisition system was clearly superior to the analog electronics. The experimental conditions used in this test were typical of most of the measurements in frequency domain fluorometry where the signal-to-noise ratio is generally about ten.

Examples

Figure 9:
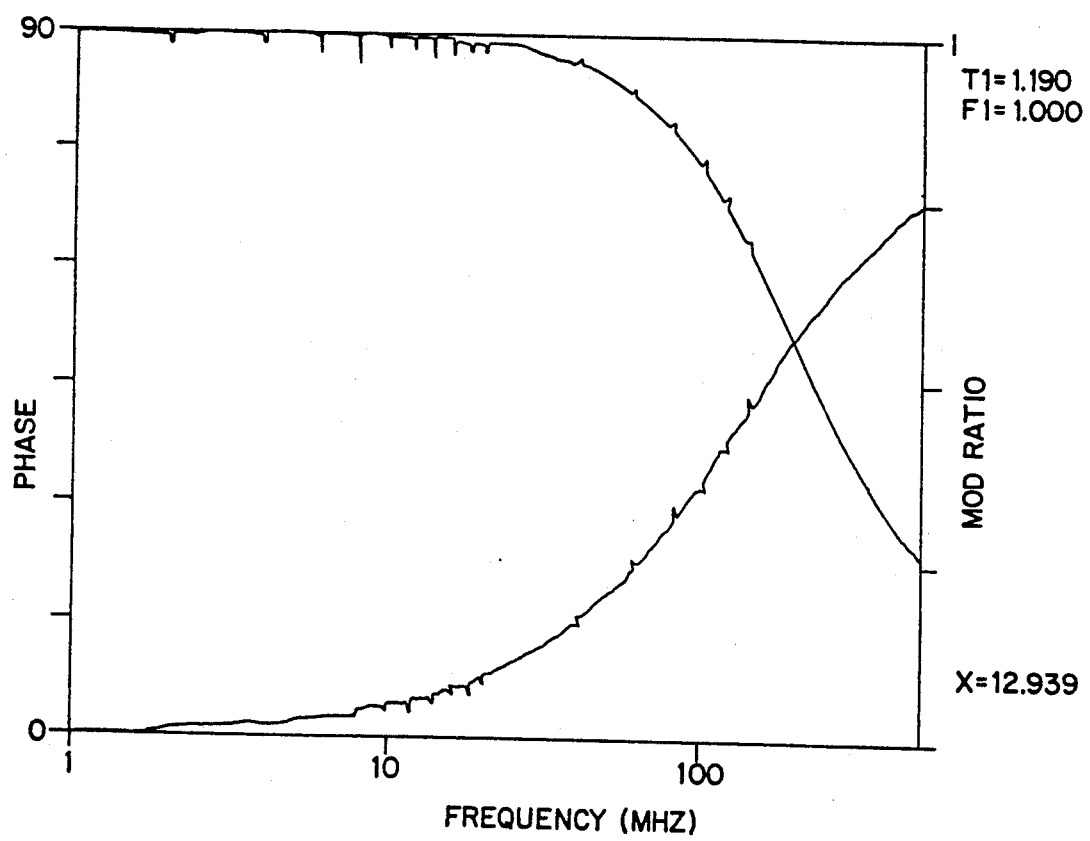
FIG. 9 is a graph illustrating the phase and modulation value of P-terphenyl obtained with the present invention.

A typical measurement from the fluorometer of the present invention is shown in FIG. 9. The phase and modulation values for a solution of P-terphenyl in alcohol are shown together with the best fit for a single exponential decay. The excitation source is a mode-locked Nd-YAG laser which synchronously pumps a dye laser (Antares model, Coherent, Palo Alto, Calif.). The output of the dye laser is cavity dumped and doubled to obtain ultraviolet (UV) light pulses. This pulse repetition rate is exactly 2.00 MHz. The quality of the data acquired in parallel, using a 10 second integration time for each of the three base frequency acquisition modes is better than the data obtained by the standard sequential mode using the analog electronic acquisition and 10 seconds integration time for each point. Note that with the parallel mode the entire decay was acquired in 60 seconds, as compared with 540 seconds effective integration time for the normal sequential mode. The actual acquisition time in the normal sequential mode was much larger (about 1000 seconds) due to the overhead time in manually setting the synthesizers to each new frequency and the need to acquire a dark current reading for every frequency.

The digital acquisition method described with respect to this invention allows for much better signal filtering than the analog electronics currently used in frequency domain fluorometers and also provides for the added capability of parallel frequency acquisition. Another advantage of the digital electronics is the intrinsic capability to modify the base filter frequency by simply entering into the computer a different number for the acquisition period. Using this possibility, we have been able to determine the best cross-correlation frequency to be used on the basis of the phase noise characteristic of the synthesizer.

Parallel Phase Fluorometer with Array Detector

Figure 2:
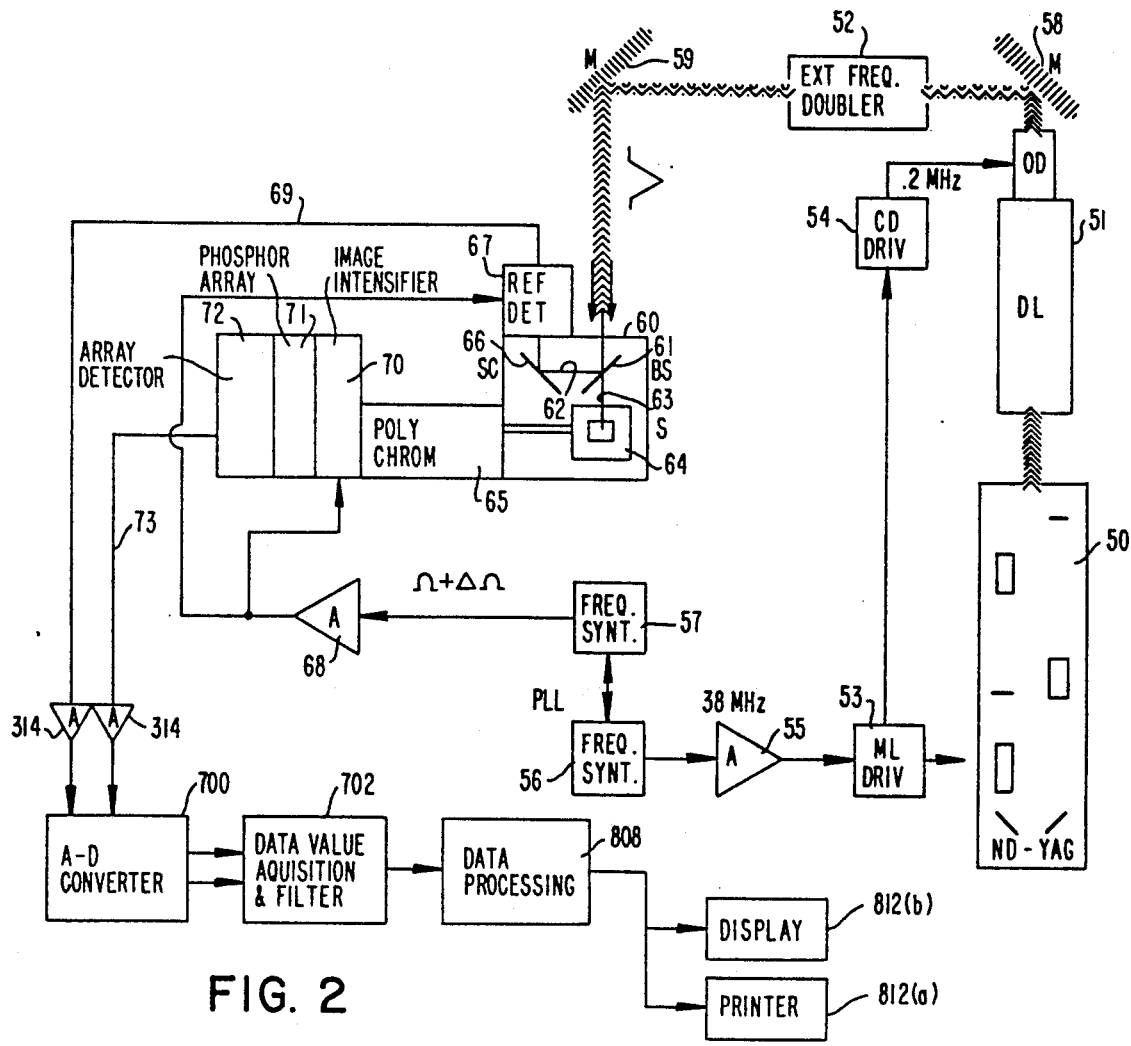
FIG. 2 is a diagrammatic illustration of a second embodiment of out invention using an improved array detector for electronic cross-correlation mixing.

FIG. 2 illustrates the parallel phase fluorometer of the present invention with a different detection and cross correlation means. As illustrated in FIG. 2, the light source is a mode locked in Nd-YAG laser 50 which synchronously pumps a cavity dumped dyelaser 51 in a manner similar to that illustrated previously with respect to FIG. 1. The pulse train out is frequency doubled to UV-light by using a frequency doubler 52. Lasers 50, 51 are driven by mode lock driver 53 and cavity dump driver 54 which are in turn driven by a radio frequency amplifier 55. Frequency synthesizer 56 provides the driving frequency for the pulsed light source, while frequency synthesizer 57 provides the driving frequency for the cross correlation means. Frequency synthesizers 56 and 57 are phase locked with a phase lock loop with frequency synthesizer 56 generating a first predetermined fundamental frequency $f_1$, and frequency synthesizer 57 generating a second frequency, which includes $f_1+f_c$ wherein $f_c$ is a correlation frequency. While $f_1$ is selected to insure a high number of intrinsic harmonics, $f_c$ is selected primarily for compatibility with the array detector as will be hereinafter further discussed.

The polarization of the dyelaser light is vertical relative to the laboratory axis while the UV output from the doubler 52 is horizontally polarized. The plane of polarization of the UV beam is rotated to 35 degrees from the vertical (the ideal polarization angle for lifetime measurements) using an arrangement of two mirrors, 58, 59, which not only change the polarization angle of the exciting light, but also steer the beam into the optical module 60. The mirrors 58, 59 have a metallic coating since a dielectric coating would give rise to wavelength and polarization dependent reflection. The pulsed light beam is split by beam splitter 61 into a reference beam 62 and a sample beam 63. The sample beam 63 impinges on a sample contained in sample holder 64 and the scattered light is passed through an aberration corrected polychromator 65 to the array detection system. The reference beam 62 is directed to a scattering surface 66, the output of which is measured by a reference detector 67 which may be a photomultiplier tube as was previously described with respect to FIG. 1. The photomultiplier 67 mixes the output of RF amplifier 68 and the signal generated by reference beam 62 to derive a reference signal on signal line 69 which is essentially the correlation signal plus any system noise or deviation not related to the sample. The array detector will be more fully described with respect to FIG. 4, it is comprised of three principle parts, image intensifier 70 a phosphorous layer 71 and a semiconductor array detector 72. In the embodiment illustrated in FIG. 2, the array detector was an Optical Multichannel Analyzer, Princeton Instruments, model IRY-512g/rb with an ISIT gatable proximity focused micro-channel plate (MCP) image intensifier, that is optically coupled to a diode array.

The array detector 72 provides a sequential analog output on signal line 73 at a preselected frequency, varying from 30 to 120 sweeps per second. The image intensifier 70 is normally used to increase the gain of the array detector 72. However, as used in the present invention, the biasing network for the image intensifier normally holds the photocathode potential at approximately 180 to 200 volts more negative than that of the potential of the microchannel electron intensifier 78. As driven by radio frequency amplifier 68, however, the cathode is driven to a gated mode wherein it is approximately 20 to 40 volts more positive than the image intensifier and effectively acts as a gate to prevent the light from the sample from reaching the array detector 72. The cathode in front of the image intensifier is gated closed at a rate $f_1 + f_c$ determined by radio frequency amplifier 68 and frequency synthesizer 57. The sample is excited at frequency $f_1$ by sample beam 63 and the emission spectrum from the sample is also varying at a frequency $f_1$, with certain phase and modulation relationship with respect to the excitation. The emission spectrum at $f_1$, and the optical gating of the image intensifier at $f_1 + f_c$ creates two optical frequencies corresponding to the sum and difference of $f_1$ and $f_c$. Since $f_c$ is selected to be relatively low, on the order of 15 Hz, a signal at this frequency is received by the array detector 72. A sweep rate of 120 sweeps per second of the array detector results in a 8X sampling of the 15 hertz correlation frequency imposed on the array detector 72 by the optical cross correlation of the image intensifier 70. Each complete cycle of the correlation frequency at 15 hertz carries the complete phase and modulation information imparted by the sample to the sample beam 63 by the emission characteristics of the sample.

The operation of the analog to digital converter, the data value acquisition programs, the averaging filter and the fast fourier transforms are essentially identical to that described for FIG. 1, with exception of the averaging or folding period. The differences relate to the differences in the filtering and averaging as necessary to accommodate the shift from 40 hertz to 15 hertz in the folding and averaging steps.

Figure 4:
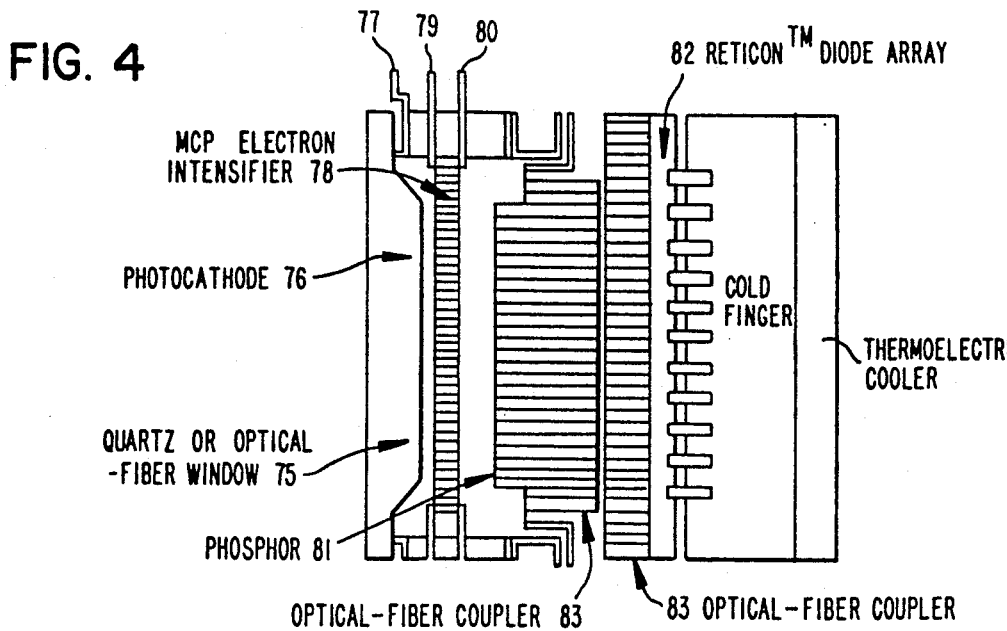
FIG. 4 is a diagrammatic illustration of the array detector used in one embodiment of the invention.

FIG. 4 illustrates in a more figurative manner, the array detector illustrated at 70-72 in FIG. 2. As illustrated in FIG. 4, the device includes a quartz or optical fiber window 75, a photocathode 76 driven by input line lead 77, a microchannel plate electron intensifier 78 which is nominally biased with in and out leads 79, 80. The array detector also includes phosphor layer 81 positioned between the image intensifier and the diode array 82. The phosphor layer and the diode array are coupled by means of an optical fiber coupler 83. The diode array 82 is a standard diode Reticon ™ detector and array by Princeton Instruments.

Figure 5:
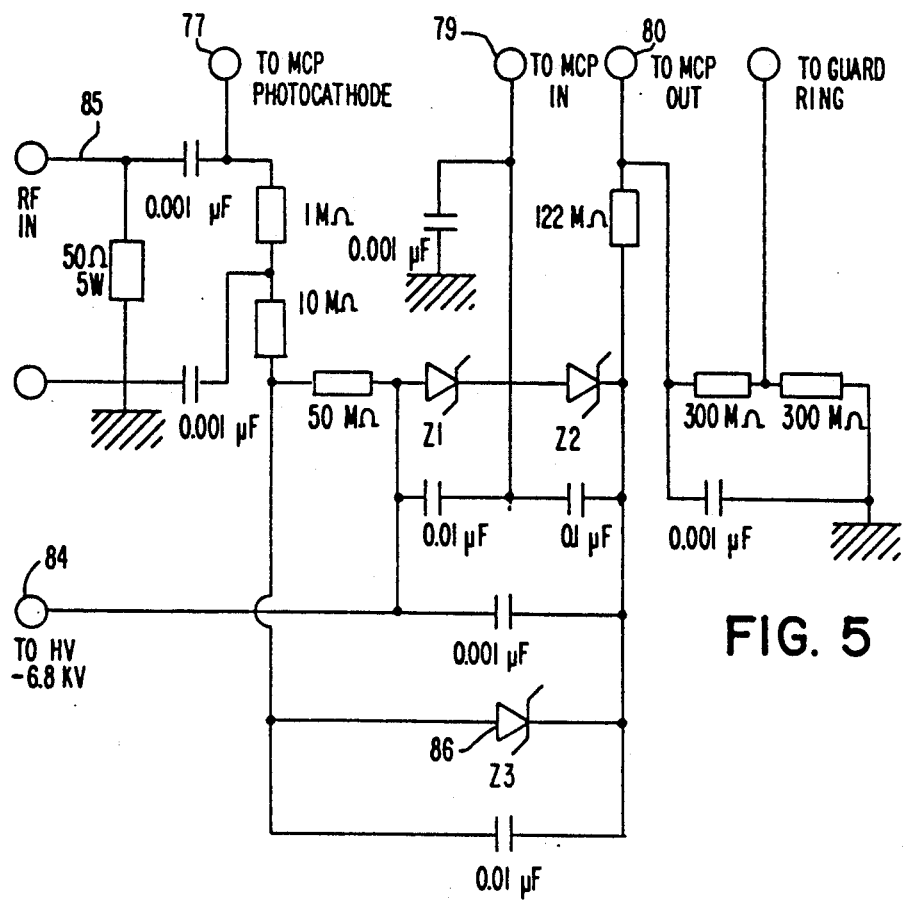
FIG. 5 is a schematic illustration of the circuit used to insert the pulse and correlation frequency into the array detector illustrated in FIG. 4.
Figure 6:
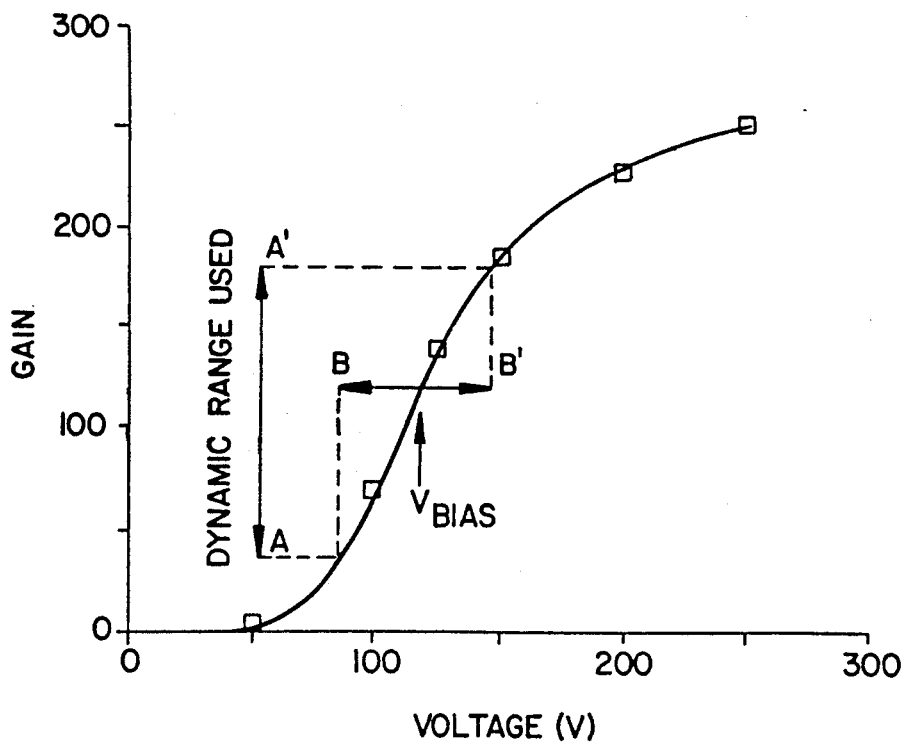
FIG. 6 a graph illustrating the preferred biasing voltage between the image intensifier and the array detector.

The biasing network for the array detector illustrated in FIG. 4 is illustrated in FIG. 5 wherein a high voltage intensifier bias is imposed at 84. The −6.8 KV is supplied by a power supply, not shown in FIG. 2, to the cathode through a series of high resistances. The resistors, not shown, are for current limiting. The dc signal path from the cathode (not through any capacitors) goes right through to Z1 and Z2. The purpose of Z1 and Z2 is to accelerate the electrons to the grid. It is important to note that this device is never really turned off. This will be explained shortly. The RF signal from amplifier 68 is inserted at 85 and the photocathode is biased as indicated at 77. The change produced by the incoming RF on the gain of the image intensifier through the acceleration voltage provides the modulation of the optical signal. The circuit illustrated in FIG. 5 is an adaptation of the original circuit provided by Princeton Instruments with the Optical Multichannel Analyzer. Zener diode 86 is added to bias the photocathode 76 to the middle of the OMA gain curve as illustrated in FIG. 6. Diode 86 is used to modify the voltage between the cathode and the MCP. The value of this diode is chosen in order to alter the gain by approximately a factor of 2. By reducing the gain by a factor of 2, the electrons are accelerated at a much lower rate in operation, the dynamic range of the OMA utilized is from approximately 40 db indicated at A to 180 db indicated at A' in FIG. 6. The use of a 90 volt Zener diode 86 provides a biasing voltage and an AC peak-to-peak voltage of approximately 60 volts as indicted by B—B' in FIG. 6. As indicated previously, the photocathode potential on line 77 is normally set by the biasing circuit to be approximately 180 to 200 volts more negative than the potential of the microchannel plate 78. By biasing the photocathode with zener diode 86, the excursions of the radio frequency input signal at 85 raise the potential of the photocathode to approximately 20 to 40 volts more positive than that of the image intensifier 78, thereby effectively gating the image intensifier and preventing any of the emissions from sample in sample holder 64 from reaching either the phosphor layer 81 or the diode array 82.

All capacitors, except for the two coming in at the RF input are used for stability purposes. The average value of the cathode voltage should not change; therefore, the capacitors are used to stabilize this average value.

The remaining two capacitors, decoupling capacitors are to prevent the −6.8 KV cathode voltage from leaking into the RF signal.

The use of the array detector, as illustrated in FIG. 2, enables the separation of emission spectrum in at least two different ways. First, the emissions may be separated by their spectral content since the OMA is connected by the polychromator 65, and the xy location of the emission can be tagged with the spectral response. Further, by combining the x,y coordinate information with the time resolved information, multidimensional information about a specific spectrum may be calculated. This information can subsequently be combined with the phase and modulation information derived by the processing means from the fast fourier transform to further assist in the separation of characteristic emissions in a mixed or multicomponent media.

Parallel array detectors (as was stated previously) are used for cross-correlation phase and modulation fluorometry, in conjunction with a modulated image intensifier; however, there are numerous other applications in which an array detector can be used. The modulation of the photo-electron current inside the intensifier is necessary to down convert or frequency translate the phase and modulation information, which is present in the fluorescence signal at high frequency typically in the mega hertz range, to a frequency typically in the hertz range, that can pass through the phosphor at the end of the intensifier and is below the Nyquist limit, which is the minimum sampling rate allowed to reconstruct a band limited waveform without error, set by the read rate of the detector. Typically, the phosphor has a decay time of 1 ms which limits the cross-correlation frequency to a value below 1 KHz. In normal photomultiplier based fluorometers, the cross-correlation frequency is at 40 Hz, so the phosphor is not a problem. The typical read rate per pixel on the phosphor is 33.33 $\mu$s and thus for a 512 linear diode array, the Nyquist limit is 30 Hz, which is also acceptable. However, for a 500×300 CCD, the Nyquist limit is on the order of a second for a digitizer rate of about 100 KHz. In applications of this type this rate is not preferrable, especially since the Nyquist limit is a theoretical limit and it is always better to over sample the signal. This means working at a maximum cross-correlation frequency of a fraction of one hertz, which is quite difficult to attain. Normally, the excitation light is modulated at a given frequency, $f_1$. Typically this is in the megahertz region. The fluorescence will also be modulated at this frequency, but the signal will be phase-shifted and demodulated with respect to the excitation light. The fluorescence light is detected with an intensifier which is modulated at $f_1$, plus a small frequency, $f_c$. The two frequencies, $f_1$ from fluorescence and $f_1+f_c$ from the modulator, will mix to produce a signal at $f_c$ with the same phase and demodulation information as the fluorescence. This frequency translation is called heterodyning. Adding another modulator or mechanical chopper, which is phase locked to the modulation frequency of the intensifier, to modulate the excitation or emission light at the cross-correlation frequency, $f_c$ is a solution to this problem. This additional signal mixes with the heterodyned signal inside the intensifier. The result is to frequency translate the heterodyned signal which is at a frequency, $f_c$, to DC. This is called homodyning. The DC signal is then detected by the diode array, or some other parallel array detector to give one point of the low frequency sine wave. The phase of the chopper modulator, is then shifted by a small amount. The amount depends on the number of points to be collected in a full wave which is 360 degrees. If 16 points per wave are to be collected, the phase must be shifted by 22.5 degrees for each run, and the DC is collected. This process is repeated until the phase is shifted a full 360 degrees. The result is a series of points that map the sinusoidal wave from which the phase and demodulation of the fluorescence signal can be derived.

Figure 2A:
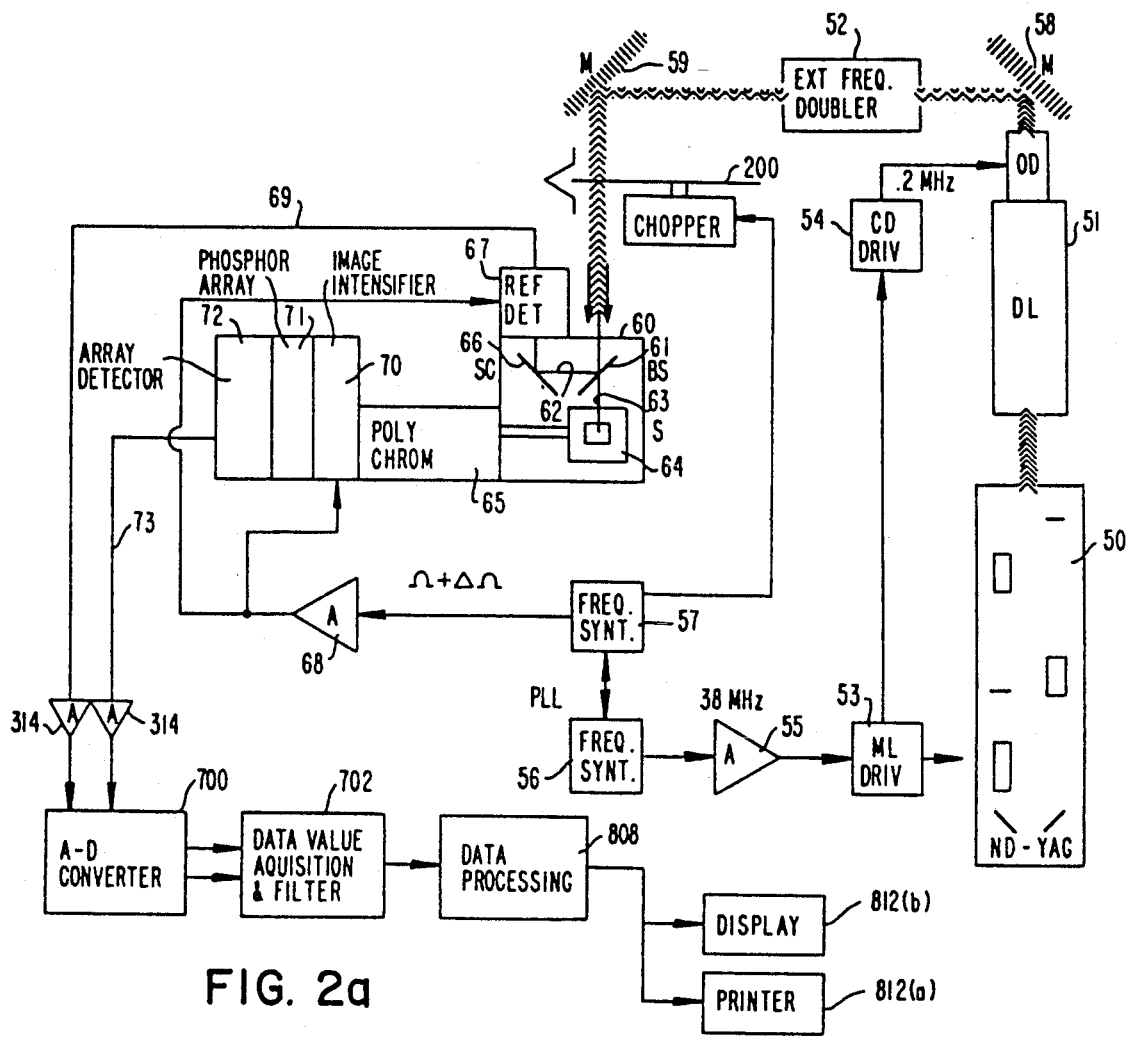

Referring to FIG. 2a, the parallel phase fluorometer utilizing the detection and cross-correlation means described in conjunction with FIG. 2 is shown incorporating the improved parallel array detector. The chopper modulator 200 is in line between the mirror 59 and optical module 60. The chopper modulator 200 receives a frequency synchronizing signal from the frequency synthesizer 57 in order to be phase locked to the modulation frequency of the intensifier 70. The chopper modulator 200 is a simple mechanical device in which rotating fins or blades allow light to pass through at a predetermined frequency based on the speed of rotation. As was indicated above, the speed of rotation is set by the frequency synchronizing signal from the frequency synthesizer 57.

There are many advantages to the above described technique. The most important is that this method makes it possible to use much higher cross-correlation frequencies. It is expensive to buy frequency generators that can operate at approximately 300 MHz with a resolution of a fraction of one hertz. The system is simplified because no new exotic parts are needed. Since the output signal is DC, the speed of the phosphor and the read rate of the detector become unimportant. A second important advantage is the use of a two-stage down-conversion process, instead of one-stage down-conversion. Theoretically, this type of measurement can be done in one stage. The intensifier can be modulated at the same frequency as the fluorescence. The result would be a DC signal that would vary with the phase difference between the phase of the signal sent to the intensifier. However, in practice, it is very difficult to set a phase difference at 100 MHz or so to an accuracy of less than on degree. This method avoids such problems by doing the homodyning at the much lower cross-correlation frequency, $f_c$.

As is stated above, the array detector is not limited to use in fluorescence measurement systems. The array detector can be utilized in systems that require light modulation or light heterodyning techniques. In these applications, fluorescence measurements are not taken, but rather modulated light which has been utilized in any number of ways.

What is claimed:

1. A digital frequency domain system for measuring the light emitted by a sample when excited by a light source having harmonic content, said system comprising:
(a) means for exciting said sample to emit a light signal, said means including a light source having a harmonic content and a predetermined fundamental frequency thereof;
(b) a first means for detecting the light emitted by the sample to generate a first electrical signal containing information representative of the response of said sample at said fundamental and harmonic frequencies;
(c) a second means for generating a second electrical signal representative of said fundamental frequency and a predetermined correlation frequency;

(d) cross-correlation means for mixing said first and second electrical signals to generate a third electrical signal having a response at the fundamental and harmonic frequencies imposed on said correlation frequency; (e) means for digitizing said third electrical signal to obtain a plurality of data values for each period of the correlation frequency;

(f) a data processing means for simultaneously calculating from said plurality of data values the phase and modulation values of the response of the sample at the fundamental and a predetermined number of said harmonic frequencies.

2. A digital frequency domain system as claimed in claim 1 wherein the system further comprises a first digital filter means for removing any non-harmonic or non-synchronous frequencies from said plurality of data values.

3. A digital frequency domain system as claimed in claim 1 wherein the light signal emitted is fluorescence.

4. A digital frequency domain system as claimed in claim 1 wherein the light signal emitted is phosphorescence.

5. A digital frequency domain system as claimed in claim 2, 3 or 4 wherein the data processing means calculates a fast fourier transform on the plurality of data values.

6. A digital frequency domain system as claimed in claim 2, 3 or 4 wherein the cross-correlation means includes photomultiplier tube.

7. A digital frequency domain system as claimed in claim 2, 3 or 4 wherein said system further comprises means for polarizing said light source before said sample is excited.

8. A digital frequency domain system as claimed in claim 2, 3 or 4 wherein said light source is pulsed at a constant frequency.

9. A digital frequency domain system as claimed in claim 2, 3 or 4 wherein said system further includes a second light detecting means for generating a reference signal at said predetermined fundamental frequency.

10. A digital frequency domain fluorometer for measuring the fluorescent response of a sample when excited by a pulsed light source, said fluorometer comprising:

(a) means for exciting said sample to emit fluorescent light, said means including a pulsed light source of a predetermined fundamental frequency, said fundamental frequency intrinsically defining a plurality of harmonic frequencies;

(b) a first means for measuring the fluorescent light emitted by the sample to generate a first electrical signal containing phase and modulation information representative of the response of said sample at said fundamental and harmonic frequencies;

(c) a second means for generating a second electrical signal representative of said fundamental frequency and a predetermined correlation frequency;

(d) cross-correlation means for mixing said first and second electrical signals to generate a third electrical signal having the phase and modulation response at the fundamental and harmonic frequencies imposed on said correlation frequency;

(e) means for digitizing said third electrical signal to obtain a plurality of data values for each period of the correlation frequency;

(f) a first filter means for removing any non-harmonic or non-synchrous frequencies from said plurality of data values;

(g) a data processing means for calculating a fast fourier transform on said plurality of data and modulation values to obtain the phase values of the response of the sample at the fundamental and a predetermined number of said harmonic frequencies;

11. A digital frequency domain fluorometer as claimed in claim 10 which further comprises means for polarizing said pulsed light source before said sample is excited.

12. A digital frequency domain fluorometer as claimed in claim 10 which further comprises means for generating a reference beam of pulsed light at said predetermined fundamental frequency, and means for generating a fourth electrical signal in response to said reference beam.

13. A digital frequency domain fluorometer as claimed in claim 12 wherein said cross-correlation means mixes said second and fourth electrical signals to generate a fifth electrical reference signal at the correlation frequency.

14. A digital frequency domain fluorometer as claimed in claim 13 wherein said means for digitizing also digitizes said fifth electrical reference signal for use by said data processing means in calculating said fast fourier transforms.

15. A digital frequency domain fluorometer as claimed in claim 10 wherein said cross-correlation means is a photomultiplier tube.

16. A digital frequency domain fluorometer as claimed in claim 11, which further comprises means for polarizing said emitted light at two orthogonal angles.

17. A digital frequency domain fluorometer as claimed in claim 16 wherein said data processing means computes the anisotropic decay from the phase and modulation values obtained from said orthogonal polarizations.

18. A digital frequency domain fluorometer as claimed in claim 10 whcrein said system further comprises means for varying the wave length of the emitted light.

19. A digital frequency domain fluorometer as claimed in claim 10 wherein said pulsed light source has a wave length in the UV range.

20. A method of measuring the response of a sample having a harmonic content when excited by a light source, said method comprising:

(a) exciting said sample to emit a light signal with a light source at a predetermined fundamental frequency, said light source having a harmonic content;

(b) detecting the light emitted by the sample to generate a first electrical signal containing information representative of the response of said sample at said fundamental and harmonic frequencies;

(c) generating a second electrical signal representative of said fundamental frequency and a predetermined correlation frequency;

(d) mixing said first and second electrical signals to generate a third electrical signal having a response at the fundamental and harmonic frequencies imposed on said correlation frequency;

(e) digitizing said third electrical signal to obtain a plurality of data values for each period of the correlation frequency;

(f) simultaneously calculating from said plurality of data values, the phase and modulation values of the response of the sample at the fundamental and a predetermined number of said harmonic frequencies.

21. A method of measuring the response of a sample as claimed in claim 20, wherein the method further includes the step of removing any non-harmonic or non-synchronous frequencies from said plurality of data values, prior to the calculation of the fast fourier transform.

22. A method of measuring the response of a sample as claimed in claim 20, wherein the light signal emitted by the sample is fluorescence.

23. A method of measuring the response of a sample as claimed in claim 20, wherein the light signal emitted by the sample is phosphorescence.

24. A method of measuring the response of a sample as claimed in claim 20 or 21 or 22 which further includes the step of polarizing the light source prior to the excitation of the sample.

25. A method of measuring the response of a sample as claimed in claim 24 which further includes the step of polarizing the emitted light at an orthogonal angle to said first polarization.

26. A method of measuring the response of a sample as claimed in claim 20 or 21 or 22 wherein the method includes the step of pulsing the light source at a constant frequency.

27. A method of measuring the response of a sample as claimed in claim 20 or 21 or 22 wherein the method further includes the steps of:
(a) generating a reference beam from said light source;
(b) mixing a fourth electrical signal generated by said reference beam with said second electrical signal to create a reference signal at the correlation frequency, and;
(c) digitizing the reference signal to obtain a plurality of reference data values to be used in calculating the phase values of the response of the sample.

28. A method of measuring the response of a sample as claimed in claim 20 or 21 or 22 wherein said excitation step is conducted with a light source having a UV wave length.

29. A method of measuring the response of a sample as claimed in claim 20 or 21 or 22 wherein said detecting step and said mixing step are conducted simultaneously with a photomultiplier tube.

30. A digital frequency domain fluorometer for measuring the response of a sample when excited by a light source, said fluorometer comprising:
(a) first means for exciting said sample to emit a light signal, said means including a light source having a harmonic content and a predetermined fundamental frequency, said light signal containing phase and modulation information representative of the response of the sample at said fundamental and harmonic frequencies;
(b) second means for generating a second signal representative of said fundamental frequency and a predetermined correlation frequency;
(c) third means for mixing said light signal and said second signal to generate a third signal representative of the phase and modulation information imposed on the correlation frequency;
(d) fourth means for converting third signal to an electrical signal and digitizing said electrical signal to obtain a plurality of data values for each period of the correlation frequency;
(e) a data processing means for simultaneously calculating from said plurality of data values phase and modulation values of the response of the sample at the fundamental and a predetermined number of said harmonic frequencies.

31. A digital frequency domain fluorometer as claimed in claim 30 wherein said third means includes an image intensifier which is gated by said second signal.

32. A digital frequency domain fluorometer as claimed in claim 31 wherein said fourth means is an array detector.

33. A digital frequency domain fluorometer as claimed in claim 30 or 31 or 32 wherein the light signal is a fluorescence signal.

34. A digital frequency domain fluorometer as claimed in claim 30 or 31 or 32 wherein the light signal is a phosphorescence signal.

35. A digital frequency domain fluorometer as claimed in claim 30 wherein said device further includes a digital averaging filter.

36. A digital frequency domain fluorometer as claimed in claim 30 or 31 or 32 or 35 wherein said data processing means calculates a fast fourier transform on the plurality of data values.

37. A digital frequency domain fluorometer as claimed in claim 36 wherein the fluorometer further includes means for polarizing the light source before the sample is excited.

38. A digital frequency domain fluorometer as claimed in claim 30 or 31 or 32 wherein the light source is pulsed at a constant frequency.

39. A digital frequency domain fluorometer as claimed in claim 30 or 31 or 32 wherein the light source is modulated at said predetermined fundamental frequency.

40. An improved array detector for detecting the emissions of an excited sample, said array detector
(a) means for exciting a sample said means exciting said sample at a predetermined frequency $f_1$;
(b) an array detector for receiving and recording the level of emissions received from sample;
(c) an image intensifier positioned between said sample and said detector;
(d) means for selectively biasing said image intensifier to effectively gate the emissions received by said detector at a frequency of $f_1$ and $f_c$;
(e) means for reading the recorded levels of emissions at the array detector at a frequency greater than $f_c$ 41. A system for measuring the light emitted by a sample when excited by a light source, said system having an array detector for detecting the modulated light emissions of an excited sample, said array detector comprising:
(a) a semiconductor array, for receiving and recording the level of modulated light emissions received from said sample;
(b) an image intensifier positioned between the sample and said semiconductor array, said image intensifier modulating the gain of the modulated light emissions received from said sample and translating said emissions from a first frequency range to a second frequency range;
(c) means for selectively biasing said image intensifier to effectively pass to said array detector emissions having frequencies of $f_1$ and $f_c$; and
(d) means for reading at a frequency than $f_c$, the recorded levels of modulated light emissions of said array detector.

42. The array detector as claimed in claim 41 further comprising means for coupling said semiconductor array with said image intensifier, said array detector translates said modulated light emissions into electrical signals while maintaining a spatial geometry equivalent to said modulated light emissions.

43. The array detector as claimed in claim 42 wherein said spatial geometry is maintained on a pixel by pixel geometry in an X-Y plane thus allowing the emissions from said sample to be studied at discrete X-Y locations.

44. The array detector as claimed in claim 43 wherein said coupling means comprises an optical fiber coupler.

45. The array detector as claimed in claim 44 wherein said semiconductor array is a charged-coupled device.

46. The array detector as claimed in claim 44 wherein said semiconductor array is a diode array.

47. The array detector as claimed in claim 41 wherein said image intensifier translates the modulated light emission received from said sample from said first frequency range to said second frequency range by modulating the gain of said emissions utilizing a radio frequency modulating signal.

48. The array detector as claimed in claim 47 wherein said first frequency range is the mega hertz frequency range and said second frequency range is the hertz frequency range.

49. The array detector as claimed in claim 48 wherein said modulation is a heterodyning technique for the frequency translation of said modulating light emissions received from said sample to a frequency range for display and recording by said array detector.

50. The array detector as claimed in claim 49 wherein said means for selectively biasing said image intensifier is a circuit for adjusting the modulation gain of said image intensifier.

51. A system for measuring the light emitted by a sample when excited by a light source, said system having an array detector for detecting the modulated light emissions of an excited sample, said array detector comprising:
(a) a semiconductor array for receiving and recording the level of modulated light emissions received from said sample;
(b) an image intensifier positioned between said sample and said semiconductor array, said image intensifier modulating the gain of the modulated light emissions from a first frequency range to a second frequency range;
(c) means for selectively biasing said image intensifier to effectively pass to said array detector emissions having frequencies of $f_1$ and $f_c$;
(d) a modulator means for further modulating said modulated light emissions from said sample at said frequency $f_c$; and
(e) means for reading at a frequency other than $f_c$, the recorded levels of modulated light emissions of said array detector.

52. The array detector as claimed in claim 51 further comprising means for coupling said semiconductor array with said image intensifier, said array detector translates said modulated light emissions into electrical signals while maintaining a spatial geometry equivalent to said modulated light emissions.

53. The array detector as claimed in claim 52 wherein said spatial geometry is maintained on a pixel by pixel geometry in an X-Y plane thus allowing the emissions from said sample to be studied at discrete X-Y locations.

54. The array detector as claimed in claim 51 wherein said image intensifier translates the modulated light emission received from said sample from said first frequency range to said second frequency range by modulating the gain of said emissions utilizing a radio frequency modulating signal.

55. The array detector as claimed in claim 54 wherein said first frequency range is the mega hertz frequency range and said second frequency range is the hertz frequency range.

56. The array detector as claimed in claim 55 wherein said modulation is a heterodyning technique for the frequency translation of said modulating light emissions received from said sample to a frequency range for display and recording by said array detector.

57. The array detector as claimed in claim 56 wherein said heterodyning technique utilizes a unique gating technique which cross-correlates a high frequency source at $f_1$ with said image intensifier at a frequency of $f_1 + f_c$ to optically cross-correlate the fluorescence emission response phase and modulation information onto $f_c$, resulting in a heterodyned signal.

58. The array detector as claimed in claim 57 wherein said modulator means is a mechanical chopper phase locked with the modulation frequency of said intensifier, a modulated output from said mechanical chopper is mixed with said heterodyned signal resulting in a DC signal.

59. The array detector as claimed in claim 58 wherein said semiconductor array detects said DC signal to record one point of a low frequency sine wave from which phase and demodulation of the emitted signal is derived.

60. The array detector as claimed in claim 58 wherein said mechanical chopper is phase shifted a predetermined number of times in order to collect a series of points of said low frequency sine wave from which phase and demodulation of the emitted signal can be derived.

61. The array detector as claimed in claim 51 wherein said means for selectively biasing said image intensifier is a circuit for adjusting the modulation gain of said image intensifier.

62. An array detector for detecting the modulated light emissions of an excited sample, said array detector comprising:
(a) a semiconductor array for receiving and recording the level of modulated light emission received from said sample;
(b) an image intensifier positioned between said sample and said semiconductor array, said image intensifier modulating the gain of the modulated light emissions from a first frequency range to a second frequency range;
(c) means for selectively biasing said image intensifier to effectively pass to said array detector emissions having frequencies of $f_1$ and $f_c$;
(d) a modulator means for further modulating said modulated light emissions from said sample at said frequency $f_c$; and
(e) means for reading at a frequency other than $f_c$, the recorded levels of modulated light emissions of said array detector.

63. The array detector as claimed in claim 62 further comprising means for coupling said semiconductor array with said image intensifier, said array detector translates said modulated light emissions into electrical signals while maintaining a spatial geometry equivalent to said modulated light emissions, said spatial geometry is maintained on a pixel by pixel geometry in an X-Y plane thus allowing the emissions from said sample to be studied at discrete X-Y locations.

64. The array detector as claimed in claim 63 wherein said image intensifier translates the modulated light emission received from said sample from the mega hertz frequency range to the hertz frequency range by modulating the gain of said emissions utilizing a radio frequency modulating signal, said modulation is a heterodyning technique for the frequency translation of said modulating light emissions received from said sample to a frequency range for display and recording by said array detector, said heterodyning technique utilizes a unique gating technique which cross correlates a high frequency source at $f_1 + f_c$ to phase and modulation information onto $f_c$, resulting in an heterodyned signal.

65. The array detector as claimed in claim 64 wherein said modulator means is a mechanical chopper phase locked with the modulation frequency of said intensifier, a modulated output from said mechanical chopper is mixed with said heterodyned signal resulting in a DC signal, said semiconductor array detects said DC signal to record one point of a low frequency sine wave from which phase and demodulation of the emitted signal is derived, said mechanical chopper is phase shifted a predetermined number of times in order to collect a series of points of said low frequency sine wave from which phase and demodulation of the emitted signal can be derived.

* * * * *

UNITED STATES PATENT AND TRADEMARK OFFICE
CERTIFICATE OF CORRECTION

PATENT NO. : 5,257,202
DATED : October 26, 1993
INVENTOR(S) : Brett A. Feddersen, et al It is certified that error appears in the above-indentified patent and that said Letters Patent is hereby corrected as shown below:

Column 5, line 26: delete "to at least"

Column 5 line 27: after "compared" insert --to at least--

Column 5, line 48: "out" should read --our--

UNITED STATES PATENT AND TRADEMARK OFFICE
CERTIFICATE OF CORRECTION

PATENT NO. : 5,257,202
DATED : October 26, 1993
INVENTOR(S) : Brett A. Feddersen, et al.

It is certified that error appears in the above-indentified patent and that said Letters Patent is hereby corrected as shown below:

Column 5, line 50: "3" should read --2A--

Column 7, line 68: "in" should read --is--

Column 10, line 20: after "cross" insert --correlation frequency by--

Column 11, line 11: after "always" insert --sufficient--

Column 24, line 64, Claim 41: after "frequency" insert --other--

Signed and Sealed this

Sixth Day of September, 1994

Attest:

BRUCE LEHMAN

Attesting Officer

Commissioner of Patents and Trademarks